United States Patent [19]

Dätwyler et al.

[11] Patent Number: 5,003,174

[45] Date of Patent: Mar. 26, 1991

[54] OPTICAL HIGH-PRESSURE TRANSMISSION CELL

[75] Inventors: Peter Dätwyler, Oberwil; Aldo Giorgetti; Peter E. Jordi, both of Basel; Nico Periclés, Herznach, all of Switzerland

[73] Assignee: Bruker Analytische Messtechnik GmbH, Fed. Rep. of Germany

[21] Appl. No.: 456,666

[22] Filed: Dec. 29, 1989

[51] Int. Cl.[5] .................... G01N 21/09; G01N 21/05
[52] U.S. Cl. .................................. 250/343; 356/246
[58] Field of Search ........................ 250/343; 356/246

[56] References Cited

U.S. PATENT DOCUMENTS 4,588,893  5/1986  Vidrine et al. ................. 250/428
4,910,403  3/1990  Kilham et al. .................. 250/343

FOREIGN PATENT DOCUMENTS 2810388   9/1978  Fed. Rep. of Germany.
2842367   4/1980  Fed. Rep. of Germany.
3305982   8/1984  Fed. Rep. of Germany.
890116   12/1981  U.S.S.R. ......................... 356/246
1183182   3/1970  United Kingdom ............. 356/246

OTHER PUBLICATIONS

I. V. Babashov, G. V. Bondarenko, Yu. E. Gorbatyl and M. B. Epel baum, "Cuvette for IR Spectroscopy of Highly Absorbing Fluids at High Pressures and Temperatures." Translated from Pirbory i Tekhnika Eksperimenta, No. 2 (Mar.-Apr., 1970), pp. 215-216.

T. R. Griffiths, F. Lee and R. H. Wijayanoyake, *J. Sci. Instrum.*, *(1967), vol. 44, pp. 876-878;* "*A simple optical cell for measuring the spectra of small amounts of volatile solutions under pressure at temperatures up to 300° C.*".

Heinz Fischer, *Z. Chem., 1, (1961), pp. 234-245;* "*Kuvetten fur spektroskopische Untersuchungen im mittleren Infrarot*".

*Primary Examiner*—Constantine Hannaher
*Attorney, Agent, or Firm*—Griffin Branigan & Butler

[57] ABSTRACT

Optical high-pressure transmission cells of the type used, for example, for SFC-FTIR, comprise a pressure-resistant housing part with two intersecting bores, one of them forming a fluid passage and the other one forming a light transmission path. The bore forming the light transmission path is provided with inserted windows. There is a demand in infrared spectroscopy, for supercritical fluid chromatography, for particularly pressure-resistant cells of simple design, which demand has not been satisfied heretofore. In the case of the proposed measuring cell, the windows are designed as stepped windows having central cylindrical neck portions engaging the bore serving as a light transmission path so that the chamber is delimited by end faces of the neck portions. Sealing is effected by O-rings.

7 Claims, 1 Drawing Sheet

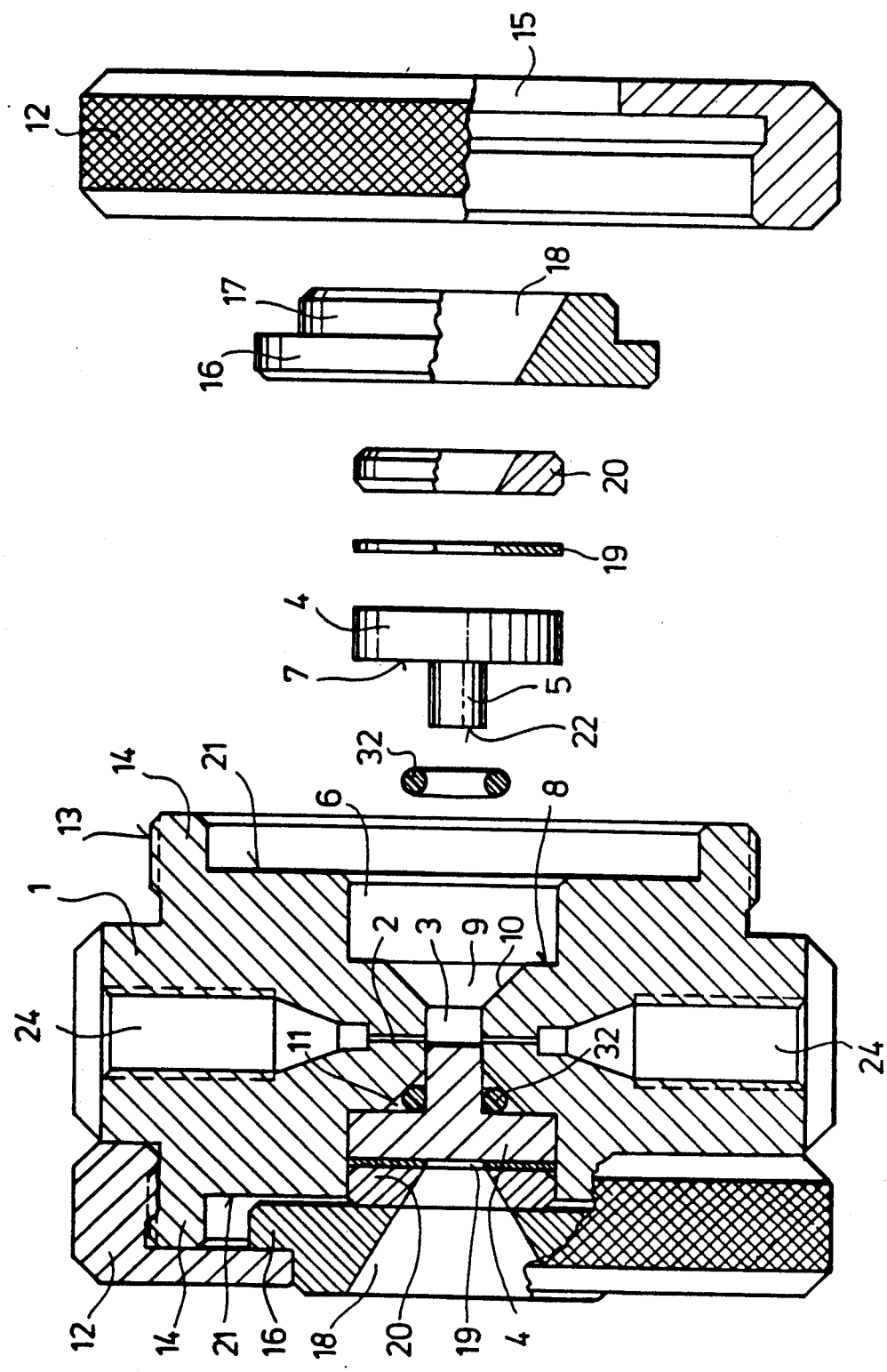

OPTICAL HIGH-PRESSURE TRANSMISSION CELL

BACKGROUND OF THE INVENTION

The present invention relates to an optical high-pressure transmission cell, preferably a measuring cell for SFC-FTIR, comprising a pressure-resistant housing element which is passed by two bores of different diameters extending perpendicularly relative to, and intersecting, each other, a thinner bore forming a passage for a highly compressed solvent containing a substance under examination, whereas a thicker bore forms a transmission path for light of an IR spectrometer, further fittings for connection of lines to ends of the thinner bore and IR-permeable windows closing off the thicker bore on both sides at points of opening of the thinner bore, each of the said windows being arranged in a recess provided in the housing part at an end of the thicker bore and being held in the said recess by a clamping body resting against an outer surface of the window and fixed to the housing part by screwing, and being sealed off relative to the housing part by means of an O-ring arranged between the housing part and the inner window surface adjoining the housing part, so that the thicker bore delimited by the windows arranged opposite each other defines a high-pressure resistant, tight chamber for the agent, or solvent containing substance passed therethrough by means of the thinner bore.

A measuring cell of this type has been known before from U.S. Pat. No. 4,588,893. A housing element of the known measuring cell comprises two plane surfaces, and recesses for receiving windows are arranged in areas of such surfaces. Outer portions of the windows extend beyond the plane surfaces and are retained in position by annular clamping bodies which are fastened to the housing element by threaded bolts. O-rings serving to seal off the windows are accommodated in annular grooves provided in bottoms of the recesses, surrounding the thicker bore in the form of a ring. The fact that the grooves for the O-rings are arranged opposite each other makes it necessary to give the housing element a considerable thickness which also determines a length of the thicker bore between the windows and, consequently, a length of a path of IR radiation through the chamber defined by the windows. In the case of the embodiment described by U.S. Pat. No. 4,588,893, the thicker bore has a length of five millimeters. In addition, the known measuring cell has a light tube inserted in this bore for establishing a connection to the opening of the thinner bore through openings provided in its periphery so that light is passed by an agent under examination in a direction perpendicular to the windows. It is another drawback of the known measuring cell that uniform tightening of the threaded bolts serving for fastening clamping bodies is very difficult because distortions may easily occur and will then stress the IR-permeable windows heavily. On the one hand, these windows are very delicate physically, so that they may easily be destroyed when stressed improperly. On the other hand, even slight distortions may change optical properties of the windows and, consequently, impair quality of IR-spectrometric measurements.

Another previously known measuring cell for SFC-FTIR is marketed by the AABSPEC companies in the U.S.A. and in Ireland under the name "MODEL 4000". According to a description given for these measuring cells, windows are arranged in a tubular body provided, in its central area, with an internal shoulder supporting the windows, preferably with a Teflon ring inserted between the windows and the shoulder. Sealing as such is effected by means of O-rings which rest against outside surfaces of the windows and which, consequently, are arranged between the windows and clamping bodies holding the windows. The exact design of these clamping bodies cannot be derived from the description of this measuring cell. However, the description warns the user not to load a central shoulder unevenly or to stress the windows excessively as this might lead to distortions and eventually to breakage of the windows. According to the description, the minimum distance achievable in this manner between the windows is equal to 0.5 mm, which distance can be increased up to 20 mm by means of spacer rings.

For a measuring cell known from U.S. Pat. No. 4,588,893, a typical pressure of a supercritical solvent is said to be between 70 and 140 bar so that it may be assumed that this measuring cell is designed for a maximum pressure of up to approx. 150 bar. As compared to this, the AABSPEC cell is intended to stand a pressure of up to approx. 280 bar (4000 psi). In fact, in cases of known measuring cells, disturbing distortions or even damage might result not only from improper clamping of windows, but also from an excessively high fluid pressure loading the windows.

Stepped windows have also been known in the prior art; this appears, for example, from DE-28 10 388 A1, DE No. 28 42 367 A1, British journal J. Sci. Instrum. 44, 1967, pages 876 to 878, and German journal Chem. 1, 1961, pages 234 to 245.

Only the two last-mentioned publications describe high-pressure measuring cells, and the purpose of the axially stepped windows illustrated in FIG. 24 on pages 241 and 242 of German journal Chem. 1, 1961 consists in reducing window openings to very small dimensions, in an area of a sample, so that crystals used for the windows, for example NaCl, can withstand the very high pressures encountered.

In contrast, DE No. 28 10 388 A1 describes a device for measuring by optical means a preselected property of a substance flowing through a line, while DE No. 28 42 367 A1 describes a device for introducing particles into analyzers for the purpose of analyzing dust content of gases.

In view of progress achieved in chromatography with supercritical phases (Supercritical Fluid Chromatography SFC) in connection with Fourier Transform IR Spectroscopy (FTIR) it would seem desirable to have a measuring cell capable of being operated at pressures of supercritical solvents of 400 bars and even more, without any risk of destruction of windows by distortions or disturbance of transmission of a light beam used for IR spectroscopy. At the same time, it is desired to have a very short light path through fluids.

SUMMARY OF THE INVENTION

Now, it is an object of the present invention to provide an optical high-pressure transmission measuring cell, preferably for SFC-FTIR, which is capable of being operated at pressures of supercritical solvents of 400 bar and more, without any risk of destruction of windows causing distortions or disturbance of the passage of the light beam used for IR spectroscopy. In addition, the invention is to allow simple adaptation of a length of the light path to a fluid in measuring chamber and to achieve a very short light path through the fluid as well.

This object is achieved according to the invention by an arrangement in which windows are stepped in the axial direction and comprise an outer portion and an inner cylindrical neck portion of smaller diameter, arranged concentrically with the outer portion, the cylindrical neck portion engaging surfaces defining a thicker bore and having an axial length corresponding to a desired length of a light path through a chamber so that the chamber is defined by end faces of the neck portions, in which each end of the thicker bore is connected with its adjoining recess by a concentrical portion widening towards the outside, and an O-ring is arranged in an annular space defined by a circumferential surface of the cylindrical neck portion, a surface of the widening portion and an inner surfaces of the outer portion of the stepped window facing the chamber. By giving the windows of the measuring cell according to the invention a stepped design it is now possible to make a distance between surfaces defining the chamber as small as desired, by convenient selection of the dimensions of the central, cylindrical neck portion, so that it is now possible to realize chambers with an extremely short light path required for certain measurements. The reinforcement of the window in its central portion, which is passed by the IR light, ensures in addition that any stresses resulting from pressures exerted upon the window are confined substantially to a clamped area of the window surrounding the cylindrical neck portion so that that part of the window which is critical for transmission of light will remain substantially free from stresses even at extremely high pressures of supercritical solvents. In addition, arrangement of the O-rings in the annular spaces formed by the widening portions also ensures perfect sealing even under very high pressures as the O-rings will settle automatically in corners formed by the inner surface of the window and the adjoining surface of the widening portion of the cell body, under the effect of the pressure. It is a particular advantage in this connection that the cross-section of the widening portion can be selected freely with a view to obtaining best possible sealing effects, because the clamping body may be given a plane contact surface for an outside surface of a window, so that the position of the window can be defined very exactly, and because the sealing effect is not dependent on a particular force being exerted by the clamping ring upon the window and a corresponding counter-surface. Instead, the clamping body now only serves the function of an abutment resting against an outer surface of the housing part and providing a support for the window whose outer surface is pressed against it by the loaded O-ring. This eliminates all risks of distortion of the window by the clamping body. According to a preferred embodiment of the invention, the widening portions are conical in shape so that the annular spaces accommodating the O-rings exhibit a triangular cross-section. One thereby obtains wedge-shaped clearances into which the O-rings are urged by the fluid pressure, which provides a particularly favorable sealing effect. In addition, according to a particularly advantageous variant, the clamping bodies may be designed as threaded rings screwed upon cylindrical shoulders of the housing surrounding the respective recess at certain distances and provided with matching outer threads. Use of such threaded rings ensures that the contact surfaces for the outsides of the windows will always remain in a position perfectly perpendicular to the axis of the bore, even during tightening of the screwing rings, so that any irregularities caused by non-uniform tightening of the windows are excluded.

In order to enable the measuring cell to be adapted to different purposes, it may be convenient not only to use windows with cylindrical neck portions of different lengths, but also to have available windows with main portions of different thicknesses. This may be desirable, for example, in order to be able to use windows made from different materials offering different pressure resistance which, therefore, must have different thicknesses. Similarly, it may be convenient to select the thicknesses of the windows as a function of the operating pressure, as the thickness of the windows has an influence on the light transmission of the IR spectroscope and should, therefore, be kept as small as possible. The use of threaded rings as clamping bodies enables the windows to be exchanged without great effort. In order to permit the use of windows of different thickness, a further improvement of the invention provides that the threaded rings are provided with pressure pieces engaging the recesses accommodating the windows which guarantees in any case exactly defined supports for the windows. One then also has the possibility to make pressure pieces exchangeable so that different pressure pieces can be used for windows of different thicknesses. However, there is also the possibility to provide a pressure piece consisting of a plurality of ring-shaped inserts guided in a central opening of the threaded ring, and/or the recess, in which case the number and/or size of the inserts can be selected according to the window used.

The invention will now be described and explained in more detail by way of the embodiment illustrated in the drawing.

SHORT DESCRIPTION OF THE DRAWING

The only figure shows one embodiment of the invention, partially as a sectional view and partially as an exploded view, in greatly enlarged scale.

DESCRIPTION OF THE PREFERRED EMBODIMENT

The measuring cell illustrated in the drawing comprises a housing part 1 consisting preferably of stainless steel and being passed by two bores 2 and 3 extending perpendicularly relative to each other and intersecting at the center of the housing part 1. The thinner bore 2 serves as passage for an eluate which contains a substance under examination and is obtained, for example, by chromatographic separation, and which is guided through such passage for the purpose of IR spectroscopy. Subsequently, the eluate may be subjected to other spectroscopic examinations. A solvent or the substance flowing through such as measuring cell may be undercritical or super-critical, depending on operating conditions. Measurements may be effected either at room temperature or at increased temperature, at a pressure of between approx. 70 and approx. 450 bar. It is, therefore, necessary that the measuring cell be sufficiently pressure-tight.

The thicker bore 3 defines the measuring cell in the passage area of the thinner bore 2, this cell being closed on both sides, in areas of openings into the thinner bore 2, by IR-permeable windows 4. In the drawing, the left side of the housing part 1 shows one window in the installed condition, while the right side of the drawing shows an exploded view of the other window.

The windows 4 consist of an IR-permeable material, for example a zinc sulfide (ZnS). They are designed as stepped windows which means that they each are provided with a central cylindrical neck portion 5. While the central neck portion 5 of each of the windows 4 engages the thicker bore 3, the remaining portion of each of the windows 4 is received in a recess 6 arranged at an outer end of the bore 3. An inner surface 7 of each of the windows 4 then rests against a bottom 8 of the matching recess 6. In addition, outer ends of the bore 3 are provided with gradually widening portions 9 of conical shape so that after insertion of the windows 4 an annular space 11 is obtained on each side between conical surfaces 10 of the widening portions 9, the circumferential surfaces of the cylindrical neck portions 5 and the inner surfaces 7 of the stepped windows 4, for accommodation of O-rings 32. The dimensions of each O-ring, which preferably consists of an ethylene-propylene copolymer, are selected in such a manner that the ring is retained in contact, at a certain tension, with all walls defining the annular space 11.

Each window 4 is held in place by a threaded ring 12 which can be screwed upon a cylindrical shoulder 14 of the housing provided with a matching outer thread 13. The threaded ring 12 comprises a central opening 15 serving to receive a ring-shaped pressure piece 16 comprising a cylindrical portion 17 of reduced diameter and bearing against an inner surface of the threaded ring 12 by its portion projecting beyond the said portion of reduced diameter 17. In addition, the ring-shaped pressure piece 16 is provided with a central opening 18 widening conically towards the outside and serving as transmission path for light.

Between an outer surface of the window 4 and the pressure piece 16, there are provided intermediate rings 19, 20, both being positioned in the recess 6 serving to receive the window 4.

As can be seen best in the left half of the drawing, when the window 4 is fitted, the rings 20 project slightly beyond an outside 21 of the housing part 1 so that an outer surface of the outer ring 20 comes into contact with an adjacent inner surface of the ring-shaped pressure piece 16 when the threaded ring 12 has been screwed home on the cylindrical shoulder, or housing portion, 14 of reduced diameter, so that the inner surface of the threaded ring 12 comes to rest against an outer surface of the cylindrical housing portion 14 of reduced diameter. The dimensions of the pressure piece 16 and the ring-shaped inserts, or intermediate rings, 19, 20 are tuned to the dimensions of the housing and the thickness of the window 4 in such a manner that the window 4 is retained in the recess 6 of the housing practically free from play, without however being subjected to an inadmissibly high pressure. Quite to the contrary, minor tolerances may even be compensated by the elasticity of the O-ring 32 loading the inner surface 7 of the window 4 in axially outward direction.

The width of the chamber in the axial direction of the thicker bore 3 is determined, obviously, by the distance between end faces 22 at ends of the central cylindrical neck portions 5 of the window. Consequently, an axial length of this chamber may be adjusted to a desired amount by appropriate selection of the dimensions of the central neck portions 5 of the windows 4. In practice, cells having a distance between the end faces 22 of 0.65 mm and 1.95 mm and, consequently, a volume of 4.6 $\mu$l and 13.8 $\mu$l, respectively, have been realized. The optical aperture was 3 mm. Using zinc sulfide windows with a diameter of 11 mm and a thickness of 3 mm, and a diameter and axial length of the central neck portion of 3 mm, trials were run at pressures of up to 450 bar, without any occurrence of damage or trouble of any kind. After replacement of the windows by metal parts, the serviceability of the cell was tested at a pressure of 600 bar, without any occurrence of damage. It is regarded as almost sure that pressures higher than 450 bar can be reached also with optical windows, by increasing the thickness of the windows and/or reducing the aperture of the window.

As has been mentioned before, a particular advantage of the invention is seen in the fact that due to their particular shape the windows enable the size of the chamber to be changed quickly, do not give rise to trouble because of distortions occurring at high pressures, and guarantee perfect tightness, even at very high pressures of the supercritical solvent, in connection with the O-ring seals 32 fitted in the annular grooves 11. Use of a screwing ring as a clamping body guarantees untwisted mounting of the windows, with the use of an abutment for the screwing ring ensuring in addition that the window cannot be subjected to inadmissibly high pressures.

It should be noted in addition that the thin bore 2 for the fluid under examination is followed by enlarged bore portions and that an outer portion 24 is provided with an internal thread for receiving screw fittings for the connection of lines.

When windows of zinc sulfide are used, as described above, the cell is serviceable in the medium IR range of 5 000 to 750 cm$^{-1}$. The cell was used, without any additional optical means, in an infrared spectrometer type IFS 88 marketed by Messrs. Bruker Analytische Messtechnik GmbH, Rheinstetten, Federal Republic of Germany. It was installed and adjusted in such a manner that the focus of an IR beam was inside the chamber. As compared with an empty measuring chamber of the spectrometer, insertion of the cell led to a reduction of transmitted radiation to 52 to 43%, depending on the aperture of the cell. During the tests, spectra were obtained of 25 $\mu$g phenyl benzoate and of 10 $\mu$g N-methyl aniline, in each case with an S/N of approx. 30. The path length was 0.65 mm. During measurements of N-methyl aniline, the aromatic C=C band was observed at 1608 cm$^{-1}$, with a resolution of 8 cm$^{-1}$.

It goes without saying that the invention is not restricted to the described embodiment, but that numerous deviations are possible without leaving the scope of the invention. Such deviations may relate specifically to the way of mounting the windows, although the illustrated embodiment of the invention is regarded as a design which gives optimum results in every respect.

The reference numerals used in the claims are not to be understood as restricting the invention, but are meant only to facilitate its understanding.

We claim:

1. An optical high-pressure transmission cell, preferably a measuring cell for SFC-FTIR, comprising a pressure-resistant housing part which is passed by two bores of different diameter extending perpendicularly relative to, and intersecting, each other, a thinner bore forming a passage for a highly compressed solvent containing a substance under examination, whereas a thicker bore forms a transmission path for light of an IR spectrometer, further fittings for connection of lines to ends of the thinner bore and IR-permeable windows closing off the thicker bore on both sides at points of opening to the thinner bore, each of said windows being arranged in a recess provided in the housing part at the end of the thicker bore and being held in said recess by a clamping body resting against an outer surface of the window and fixed to the housing part by screwing, and being sealed off relative to the housing part by means of an O-ring arranged between the housing part and an inner window surface adjoining the housing part, so that the thicker bore delimited by the windows arranged opposite each other defines a high-pressure resistant, tight chamber for the substance passed therethrough by means of the thinner bore, wherein:

said windows (4) are stepped in an axial direction of said thicker bore and comprise each an outer portion and an inner cylindrical neck portion (5) of smaller diameter, arranged concentrically with said outer portion, said cylindrical neck portion positioned in said thicker bore (3) and having an axial length corresponding to a desired length of a light path through said chamber so that said chamber is defined by end faces (22) of said neck portions (5), wherein each end of said thicker bore (3) is connected with an adjoining recess (6) by a concentrical portion (9) widening towards the outside, and said O-ring (32) is arranged in an annular space (11) defined by a circumferential surface of said cylindrical neck portion (5), a surface of said widening portion 9 and an inner surface (7) of the outer portion of said stepped window (4) facing the chamber.

2. Measuring cell according to claim 1, wherein said widening portion (9) is conical in shape so that said annular space (11) accommodating said O-ring (32) exhibits a triangular cross-section.

3. Measuring cell according to claim 2, wherein said clamping body (12) is designed as a threaded ring screwed upon said cylindrical shoulder (14) of said housing surrounding the respective recess (6) at a certain distance and provided with a matching outer thread (12), wherein said threaded ring (12) is provided with a pressure piece (16, 19, 20) guided in said recess, and wherein said pressure piece (16, 19, 20) consists of a plurality of ring-shaped inserts guided in said central opening (15) of said threaded ring (12), and/or said recess (6).

4. Measuring cell according to claim 1, wherein said clamping body (12) is designed as a threaded ring screwed upon said cylindrical shoulder (14) of the housing surrounding the respective recess (6) at a certain distance and provided with a matching outer thread (12).

5. Measuring cell according to claim 4, wherein said threaded ring (12) is provided with a pressure piece (16, 19, 20) positioned in said recess.

6. Measuring cell according to claim 5, wherein said pressure piece (16, 19, 20) consists of a plurality of ring-shaped inserts guided in a central opening (15) of said threaded ring (12), and/or said recess (6).

7. Measuring cell as in claim 1 wherein the concentrical portion gradually widens towards the outside.

* * * * *